United States Patent [19]

Dirlam et al.

[11] Patent Number: 5,206,263
[45] Date of Patent: Apr. 27, 1993

US005206263A

[54] ACIDIC POLYCYCLIC ETHER USEFUL AS AN ANTICOCCIDIAL AGENT AND AS A GROWTH PROMOTANT

[75] Inventors: John P. Dirlam, Gales Ferry; Walter P. Cullen, East Lyme, both of Conn.; Hiroshi Maeda; Junsuke Tone, both of Chita, Japan

[73] Assignee: Pfizer Inc., New York, N.Y.

[21] Appl. No.: 438,506

[22] PCT Filed: Jun. 24, 1987

[86] PCT No.: PCT/US87/01487

§ 371 Date: Dec. 5, 1989

§ 102(e) Date: Dec. 5, 1989

[51] Int. Cl.$^5$ .............. C07D 311/96; C12P 17/18; A61K 31/35
[52] U.S. Cl. .............. 514/460; 514/25; 549/343; 435/119; 435/118; 435/74; 435/898; 435/886; 536/126
[58] Field of Search ......... 435/119, 118, 79, 898, 435/886; 514/25, 449; 549/343; 536/126

[56] References Cited

U.S. PATENT DOCUMENTS

| | | | |
|---|---|---|---|
| 3,577,531 | 10/1981 | Gorman et al. | 435/119 |
| 4,150,152 | 4/1979 | Celmer et al. | 424/122 |
| 4,293,650 | 10/1981 | Florent et al. | 435/119 |
| 4,366,311 | 12/1982 | Mizutani et al. | 536/123 |
| 4,427,655 | 1/1984 | Stapley | 424/115 |
| 4,504,584 | 3/1985 | Kitaura et al. | 435/253 |
| 4,591,559 | 5/1986 | Liu et al. | 435/76 |

OTHER PUBLICATIONS

Hamill et al., J. Antibiotics (Japan), vol. 22, pp. 161-164 (1969).
Liu et al., J. Antibiotics (Japan), vol. 29, 21-28 (1976).
Perry, Chemical Engineers' Handbook, Fifth Edition, pp. 20-58 to 20-63, (1973).

*Primary Examiner*—Irene Marx
*Attorney, Agent, or Firm*—P. C. Richardson; G. C. Benson; A. D. Olson

[57] ABSTRACT

An acidic polycyclic ether antibiotic, having structure established by X-ray crystallography, is formed by fermentation of a novel microorganism, *Streptomyces hygroscopicus* ATCC 53626. This novel antibiotic is useful as an anticoccidial in chickens and as a growth promotant in cattle and swine.

8 Claims, No Drawings

ACIDIC POLYCYCLIC ETHER USEFUL AS AN ANTICOCCIDIAL AGENT AND AS A GROWTH PROMOTANT

BACKGROUND OF THE INVENTION

The present invention concerns a new acidic polycyclic ether antibiotic having the absolute stereochemical formula

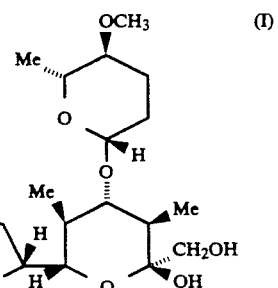
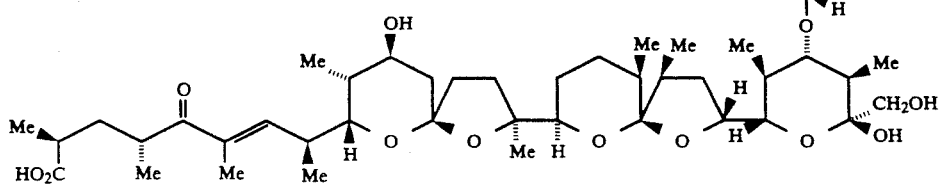

wherein Me=CH$_3$; pharmaceutically acceptable cationic salts thereof; nutrient feed compositions comprising said antibiotic for poultry, cattle or swine; it use as an anticoccidial agent in poultry, or as a growth promotant in cattle or swine; a fermentation method for its preparation; and the *Streptomyces hygroscopicus* microorganism which produces said antibiotic in said fermentation method.

The compound (I) is a new member of the acidic polycyclic ether group of antibiotics. This family includes such well known agents as monensin (The Merck Index, 10th Ed., Merck and Co., Inc., Rahway, N.J., 1983, monograph no. 6100), nigericin (loc. cit., monograph no. 6390), narasin (loc. cit., monograph no. 6271), lasalocid (loc. cit., monograph no. 5204), and salinomycin (loc. cit., monograph no. 8193). The subject has been reviewed by Westley, "Polyether Antibiotics", Adv. Appl. Microbiol., vol. 22, pp. 177–223 (1977). These compounds are generally known as coccidiostats and/or as feed additive-growth promotants.

SUMMARY OF THE INVENTION

A culture of *Streptomyces hygroscopicus*, ATCC 53626, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said *S. hygroscopicus* ATCC 53626 in an aqueous nutrient medium comprising an assimilable source of carbon and nitrogen until a recoverable amount of said compound of the formula (I) is formed, preferably under submerged aerobic conditions. For use as an anticoccidial agent and/or a growth promotant, the compound (I) is not necessarily separated from the fermentation and isolated in substantially pure form, but is alternatively used in crude form, either in precipitated form admixed with mycelium (recovered by filtration of the fermentation medium), or in solids obtained by spray- or freeze-drying the entire fermentation medium.

Said pharmaceutically-acceptable cationic salts include, but are not limited to, those of sodium, potassium, calcium, ammonia, N,N'-dibenzylethylene-diamine, N-methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote growth and/or improve the feed utilization of said cattle or swine, and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; and to a method for controlling coccidial infections in poultry which comprises administering to said poultry an anticoccidially effective amount of the compound of the formula (I), particularly in the form of a nutrient feed composition.

Finally, the present invention is directed to a biologically pure culture of *Streptomyces hygroscopicus* ATCC 53626, said culture being capable of producing the compound of the formula (I) in a recoverable quantity upon fermentation in an aqueous nutrient medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated *Streptomyces hygroscopicus*, and has been deposited in The American Type Culture Collection, Rockville, Md. as the type culture under their accession number ATCC 53626. Permanency of the deposit of this culture at The American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

This novel culture was derived from a soil sample collected in Aba, Nigeria, and identified in the culture collection of Pfizer Inc. as N753-21. Its description and classification were provided by Dr. L. H. Huang. This culture was found to produce narrow dimensions of the hyphae, an aerial mycelium, an unfragmented substrate mycelium and spores borne in chains on the aerial mycelium. A slant culture of the microorganism was planted into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the result read at varying times, but most commonly at fourteen days. The colors were described in common terminology, but exact colors were determined by comparisons with color chips from *The Color Harmony Manual*, fourth edition. The methods of whole-cell amino acid and sugar analyses are those described in Becker et al., Appl. Microbiol., vol. 12, pp. 421-423 (1964) and in Staneck et al., Appl Microbiol., vol. 28, pp. 226-231 (1974).

The culture was identified as follows:

Yeast Extract-Malt Extract Agar (ISP #2 medium, Difco)—Growth good, pale gray to tan (near gray series 2 cb, 3 ie); raised, wrinkled, with pale gray aerial mycelium; reverse yellowish brown (3 ic); soluble pigment yellowish brown (3 lc).

Oatmeal Agar (ISP #3 medium, Difco)—Growth moderate, white, pale gray, pale grayish yellow to pale yellowish brown (near gray series 3 cb, 3 dc, 2 gc, 3 gc); slightly raised, smooth, with white to pale gray aerial mycelium; reverse pale grayish yellow to pale yellowish brown (2 gc, 3 gc); soluble pigment pale yellowish (2 ea).

Inorganic Salts-Starch Agar (ISP #4 medium, Difco)—Growth moderate, yellowish gray (2 ie), slightly raised, smooth, aerial mycelium none or sparse, pale gray (near gray series 3 cb), reverse pale grayish yellow (2 gc), no soluble pigment.

Glycerol-Asparagine Agar (ISP #5 medium, Difco)—Growth poor, cream (1 1/2 ca); thin, smooth, no aerial mycelium; reverse cream (1 1/2 ca); no soluble pigment.

Czapek-Sucrose Agar (Waksman, "The Actinomycetes", v. 2, medium #1, p. 328, 1961)—Growth moderate, pale grayish cream (near 2 ec); slightly raised, smooth, no aerial mycelium; reverse same as surface, soluble pigment cream (2 ca).

Glucose-Asparagine Agar (ibid., medium #2)—Growth good, white to pink gray (near gray series 5 dc, fe), moderately raised, smooth, granular to wrinkled, with white to pink gray (near gray series 5 dc, 5 fe) aerial mycelium; reverse yellowish to pink gray (2 ga, near gray series 5 dc); soluble pigment cream (2 ca).

Gordon and Smith's Tyrosine Agar (Gordon and Smith, J. Bact., 69:147-150, 1955)—Growth moderate, yellowish brown to dark brown (3 gc, 4 lg); slightly raised, smooth to slightly wrinkled, no aerial mycelium, reverse brown (4 le); soluble pigment dark brown (4 ng, 4 lg).

Calcium Malate Agar (Waksman, Bact. Rev. 21, 1-29, 1957)—Growth poor to moderate, cream (2 ca), thin, smooth, no aerial mycelium, reverse cream (2 ca), no soluble pigment.

Casein Agar (Gordon and Smith, ibid.)—Growth good, brown (4 ie); raised, wrinkled, no aerial mycelium; reverse brown (3 ic, 3 le); soluble pigment brown (4 ne).

Bennett's Agar (Waksman, loc. cit., medium #30, p. 331)—Growth good, tan to yellowish brown (3 gc, 3 ie); moderately raised, slightly wrinkled; aerial mycelium sparse, white to pale gray (near gray series 3 cb, 3 dc); reverse same as surface; no soluble pigment.

Emerson's Agar (ibid., medium #28, p. 331)—Growth good, tan (3 ie); moderately raised, smooth to slightly wrinkled, no aerial mycelium; reverse tan; soluble pigment yellowish brown (3 lc).

Nutrient Agar (ibid., medium #14, p. 330)—Growth moderate, cream (2 ca); thin to slightly raised, smooth, no aerial mycelium; reverse cream (2 ca); no soluble pigment.

Gelatin Agar (Gordon and Mihm, J. Bact. 73, 15-27, 1957)—Growth moderate to good, grayish yellow (2 gc); moderately raised, smooth to wrinkled, no aerial mycelium; reverse grayish yellow to pale yellowish brown (2 gc, 3 gc); no soluble pigment.

Starch Agar (ibid.)—Growth good, yellowish brown to brown (3 gc, 3 ie); moderately raised, wrinkled, no aerial mycelium; reverse yellowish brown to reddish brown (3 gc, 4 gc); no soluble pigment.

Potato Carrot Agar (Lechevalier, Lab. Clin. Med., 71, 934-944, 1968, but use only 30 g. potatoes, 2.5 g. carrots and 20 g. agar)—Growth poor to moderate, cream (2 ca); slightly raised, smooth, no aerial mycelium; reverse colorless to cream (2 ca); no soluble pigment.

Tap Water Agar (2%)—Growth poor, colorless to cream (2 ca); thin, smooth, no aerial mycelium, reverse same as surface; no soluble pigment.

Morphological Properties—The morphological properties were observed on glucose-asparagine agar after fifteen days of incubation, spore mass in the Gray color-series, appearing as hygroscopic patches in some areas, spore chains in Section Spirales, tightly coiled or slightly open, up to six turns, of small diameters, 10 to 30 spores per spore chains; sporophores monopodially branched; spores oval to elliptical, $1.2-1.8 \times 0.8-1.1$ mcm; spores warty, as revealed by scanning electron microscopy.

Biochemical Properties—Melanin not produced; hydrogen sulfide produced; gelatin liquefied; starch hydrolyzed; nitrate not reduced to nitrite; poor growth on Jensen's cellulose but good growth on Levine and Schoenlein's cellulose; no degradation on both cellulose broths; no coagulation but clearing on milk; casein digestion positive; calcium malate digestion positive; tyrosine digestion positive. Carbohydrate utilization; glucose, arabinose, fructose, inositol, mannitol, raffinose, rhamnose, sucrose and xylose all utilized.

| Temperature Relations | | | |
|---|---|---|---|
| 21° C. | 28° C. | 37° C. | 45° C. |
| Good Growth | Good Growth | Moderate to Good Growth | No Growth |

Cell Wall Analyses—The whole-cell hydrolysates contained LL-diaminopimelic acid, glucose and galactose.

The culture N753-21 is characterized by the negative melanin reaction, the gray aerial mycelium, the spiral spore chains, and the spores with a warty surface. It utilizes all the sugars. The whole-cell hydrolysates contain LL-diaminopimelic acid but no diagnostic sugars. On glucose-asparagine agar, the aerial mycelium aggregates into hygroscopic masses in some areas. Except for positive utilization of sucrose and raffinose, the culture fits into the description of the neotype strain of *S. hygroscopicus* published in Int. Syst. Bacteril., 22:265-394, 1972. The utilization of carbon sources differs among strains according to H. D. Tresner and E. J. Backus, who proposed a broadened concept of the species (see Appl. Microbiol. 4:243-250, 1956). The culture N753-21 is thus considered as a new strain of *Streptomyces hygroscopicus* (Jensen) Waksman and Henrici.

The antibiotic compound (I) of the present invention is readily produced by the *Streptomyces* culture by growing at from about 24° to about 36° C. under submerged conditions with agitation and aeration on media consisting of carbohydrate sources such as sugars, starches, glycerol; organic nitrogen substances such as soybean meal, casamino acids, yeast extract; growth substance such as grain solubles, fish meal, cotton seed meal; mineral salts containing trace elements such as iron, cobalt, copper, zinc, etc. and calcium carbonate or phosphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, inoculum is first prepared by scraping vegetative cells, growing on a suitable media, from slants or Roux bottles which have been inoculated with the *Streptomyces* culture. The resulting vegetative cells are in turn used to inoculate shake flasks or inoculum tanks, also containing suitable growth media. Alternatively, the inoculum tanks are inoculated from the shake flasks. Following a suitable growth period (e.g., 72-96 hours), the fermentor, also containing suitable growth media, is inoculated with vegetative broth from the shake flasks or inoculum tanks. Upon completion of growth (e.g., 72-120 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, *Acta. Pathologica et Microbiologia Scandinav*, Supp. 217, Section B: 64-68 [1971]), and employs brain heart infusion (BHI) agar and an inocula replicating device. Overnight growth tubes are diluted 100 fold for use as the standard inoculum (20,000-10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Like other polycyclic ether antibiotics, the present compound of the formula (I) typically shows Gram positive antibacterial activity, as illustrated in Table (I).

TABLE I

IN VITRO ANTIBACTERIAL ACTIVITY OF THE COMPOUND OF THE FORMULA (I)

| Organism | Strain No. | MIC, mcg/ml |
|---|---|---|
| *Clostridium perfringens* | 10A006 | 1.56 |
| | 10A009 | 1.56 |
| *Actinomyces pyogenes* | 14D002 | 1.56 |
| | 14D008 | 0.78 |
| | 14D011 | 1.56 |
| *Treponema hyodysenteriae* | 94A001 | 0.39 |
| | 94A002 | 0.39 |
| | 94A007 | 0.39 |
| | 94A008 | 0.39 |

Efficacy data for the compound of the formula (I) and its salts against coccidial infections in chickens is obtained by the following method. Groups of 3-5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3-5 ten-day old chicks are fed a similar mash diet without compound (I) or its salts. They are also infected after 24 hours and serve as infected controls Yet another group of 3-5 ten-day old chicks are fed the same mash diet without antibiotic and are not infected with coccidia. These served as normal controls. The results of treatment are evaluated after five days in the case of *E. acervulina*, and six days for all other challenges.

The criteria used to measure anticoccidial activity consists of lesion scores of 0 to 4 for *E. tenella* after J. E. Lynch, "A New Method of the Primary Evaluation of Anticoccidial Activity", *Am. J. Vet. Res.*, 22, 324-326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", *Exp. Parasit.*, 28, 30-36, 1970. Activity is measured by dividing the lesion score of each treated group by the lesion score of the infected control. In this test, the compound (I) and its cationic salts exhibit excellent activity against *Eimeria tenella*, *E. acervulina*, *E. maxima*, *E. brunetti* and *E. necatrix* infections in poultry when incorporated into the mash diet of chickens at levels of 30 to 120 ppm.

For the prevention or control of coccidiosis in poultry, the compound of this invention is orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate, or added directly to the feed as such, or in the form of a premix or concentrate. A premix or concentrate of therapeutic agent in a carrier is commonly employed for the inclusion of the agent in the feed. The therapeutic agent can be in substantially pure form (e.g., the free acid, or a pharmaceutically-acceptable salt thereof), in assayed crude from such as wet or dry mycelium or dried whole broth. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements are added directly to the poultry feed to product a nutritionally balanced, finished feed containing a therapeutically effective level of one or more of the compounds of this invention. The mixtures are thoroughly blended by standard procedures, such as in a twin shell blender, to ensure homogeneity.

For use in poultry, the use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of 15 to 150 ppm. When administered in drinking water, the level which will be that which will provide the same daily dose of medication, i.e. 15 to 150 ppm, factored by the weight ratio of the average daily consumption of feed to the average daily consumption of water.

The activity of the compound of the formula (I) and its salts in promotion growth and/or increasing the efficiency of food utilization is swine or cattle can be measured directly by feeding test groups of animals various levels of the compound (I) or a salt in feed. However, a more convenient technique is described in British Patent Specification No. 1,197,826, which details an in vitro rumen method for the evaluation of feeds. The changes occurring in feed, brought about by microorganisms, are thereby readily measured with great accuracy. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content of the rumen fluid indicates that a desirable response to overall ruminant performance has been brought about by the growth promotant in the feed composition. The change in propionic acid content is expressed as percent of the propionic acid content found in the control rumen fluid. Long term in vivo feeding studies have shown a reliable correlation between propionic acid increase in the rumen fluid and improved animal performance, whether ruminant (e.g. cattle, sheep) or monogastric (e.g. swine).

In detail, rumen fluid is collected from a fistulated cow which is fed on a commercial fattening ration plus hay. The rumen fluid is immediately filtered through cheese cloth, and 10 ml. added to a 50 ml. conical flask containing 400 mg. of standard substrate (68% corn starch +17% cellulose+15% extracted soybean meal), 10 ml. of a pH 6.8 buffer and the test compound. The flasks are gassed with oxygen free nitrogen for about two minutes, and incubated in a shaking water bath at 39° C. for about 16 hours. All tests are conducted in triplicate. After incubation, 5 ml. of the sample is mixed with 1 ml. of 25% metaphosphoric acid. After 10 minutes 0.25 ml. of formic acid is added and the mixture centrifuged at 1500 rpm for 10 minutes Samples are then analyzed by gas-liquid chromatography by the method of D. W. Kellog, J. Dairy Science, 52, 1690, 1969. Peak heights for acetic, propionic and butyric acids are determined for samples from untreated and treated incubation flasks.

When tested by this in vitro procedure, the compound of the formula (I) at a level of 10 micrograms per milliliter gave rise to an increase of about 60% in the production of propionic acid over that produced in the control solution without added compound (I).

For use in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I) in cattle or swine feed will generally be in the range of 5 to 50 ppm. In ruminants the compound of the formula (I) can also be orally administered in the form of a bolus which is retained in the rumenoreticular sac, releasing the therapeutic agent at a substantially constant rate over a prolonged period of time, e.g., 4–8 weeks, providing a dose equivalent to the above 5 to 50 ppm in feed, i.e.:

$$\left(\begin{array}{c}\text{average daily dose}\\ \text{in milligrams}\end{array}\right) = \left(\begin{array}{c}5 \text{ to } 50\\ \text{ppm}\end{array}\right) \times \left(\begin{array}{c}\text{average daily feed}\\ \text{consumption in Kg}\end{array}\right).$$

Exemplary of such a controlled release bolus is that of Cardinal, U.S. Pat, No. 4,601,893.

The present invention is illustrated by the following examples. However, it should be understood that the invention is not limited to the specific details of these examples.

EXAMPLE 1

Fermentation of *Streptomyces hygroscopicus* ATCC 53626

The *Streptomyces* was initially grown by inoculating solid media on slants or Roux bottles with the ATCC 53626 culture, using ATCC medium No. 172, prepared and having composition as follows.

|  | Grams/liter |
| --- | --- |
| Glucose | 10 |
| Soluble Starch | 20 |
| Yeast Extract | 5 |
| Casein Enzymatic Hydrolysate | 1 |
| Calcium Carbonate | 1 |
| Distilled Water to 1000 ml; pH to 7.0 with KOH; Add Agar | 20 |

Meanwhile, shake flasks were prepared using one or the other of the following media:

| C' | Grams/ liter | JDY TT | Grams/ liter |
| --- | --- | --- | --- |
| Cerelose | 0 | Cerelose | 10 |
| Soy Flour | 10 | Corn Starch | 5 |
| Corn Ferm Prod | 5 | Corn Steep Liquor | 5 |
| Corn Starch | 10 | Casein Enzymatic Hydrolysate | 5 |
| Sodium Chloride | 5 | Cobalt Chloride | 0.002 |
| Cobalt Chloride | 0.002 | Calcium Carbonate | 3 |
| Calcium Carbonate | 1 | | |

One hundred ml of medium was distributed into 300 ml shake flasks and sterilized at 120° C. and 15 p.s.i. for 30 minutes. After cooling, the medium was inoculated with a vegetative cell suspension scraped from the above *Streptomyces* slant culture. The flasks were shaken at 28° C. on a shaker having a displacement of 1.5 to 2.5 inches and 150 to 200 cycles per minute (CPM) for three to four days.

Meanwhile, 5 liter fermentation vessels were prepared containing 3 liters of one of the following media:

| C' | Grams/ liter | JDY TT | Grams/ liter |
| --- | --- | --- | --- |
| Cerelose | 10 | Cerelose | 10 |
| Corn Starch | 10 | Corn Starch | 5 |
| Soybean Flour | 10 | Corn Steep Liquor | 5 |
| Corn Ferm Solids | 5 | Cobalt Chloride | 0.002 |
| Sodium Chloride | 5 | Casein Enzymatic Hydrolysate | 5 |
| Cobalt Chloride | 0.002 | Calcium Carbonate | 3 |
| Calcium Carbonate | 1 | | |

An antifoaming agent (polypropyleneglycol, MW2000, containing 10% ethylene oxide by weight, 1 ml) was added, and the vessels were sealed and sterilized at 120° C. and 15 p.s.i. for 45 minutes. The vessels were then inoculated with one shake flask (ca 3% inoculum), fermented for 96 to 144 hours at 30° C., stirring at 1700 revolutions per minute (RPM) with an air rate of one volume of air per volume of liquid per minute.

When the fermentation was completed (based on an antibiotic disc assay versus *B. subtilis* ATCC 6633) the fermentors were stopped and filtered at the natural pH with the aid of a diatomaceous earth. The filter cake was slurried in methanol, concentrated in vacuo, diluted with 2-3 volumes of water then extracted 2× with ⅓ to ¼ volume of either methylisobutyl ketone or n-butanol. The solvent layer was separated from the aqueous phase by aspiration or centrifugation, sparkled and concentrated in vacuo to the antibiotic of the formula (I) in crude form as a viscous oil.

The bioactivity of the broth and subsequent recovery streams can be followed by using a sensitive strain of *Bacillus subtilis* ATCC 6633 or *Staphylococcus aureus* ATCC 6538. The components in the broth and recovery streams can be visualized by using Analtech silica gel GF plates employing ethyl acetate as eluant. The developed plates are sprayed with vanillin reagent (3 g vanillin in 75 ml ethanol and 25 ml 85% phosphoric acid) and heated to 80° C. The antibiotic product of the formula (I) appears as a reddish spot. The developed tlc plate can also be overlayed with agar seeded with either *S. aureus* or *B. subtilis* to which 2,3,5-triphenyl-2H-tetrazolium chloride monohydrate has been added and incubated at 37° C. for 16 hours to visualize the antibiotic (white spots against a pink background).

Scale-up in large fermentors was carried out by preparing shake flasks containing 0.7 liters of C' or JDY TT medium. The shake flask inoculum was fermented for 3 to 5 days at 28° C., and used to inoculate a 200 liter fermentor containing 100 liters of C' medium. Approximately one liter of inoculum was used in the tank. The fermentor, after fermenting 5 to 7 days, was harvested. The whole broth was extract with ⅓ volume of methylisobutyl ketone at natural pH, separated on an alpha DeLaval separator and the solvent concentrated in vacuo to a crude antibiotic of the formula (I) as an oil (185 g.).

EXAMPLE 2

Isolation of the Antibiotic Compound of the Formula (I)

The crude product of the large scale fermentation of the preceding Example (185 g.) was triturated with hexane. The hexane soluble material (150 g. following concentration in vacuo) was purified using high pressure liquid chromatography (HPLC). HPLC was carried out on a Waters micro Bondapak C18 column using methanol—water (90:10) followed by HPLC on a silica gel column using methylene chloride—ethanol (96:4). The eluates were examined by thin-layer chromatography on silica gel plates developed with chloroform—isopropanol (95:5), then sprayed with 3.3% vanillin dissolved in ethanol—phosphoric acid (2:1). Upon heating to 80° C. the desired antibiotic compound (I) appeared as a reddish pink spot at Rf 0.19. Fractions containing the compound (I) were combined and evaporated to dryness to give 33.0 g. of the desired product. The hexane insoluble material (35 g) was chromatographed on a column grade silica gel column eluted with ethyl acetate. Fractions containing the compound (I) were further purified by HPLC on a silica gel column eluting with methylene chloride—ethanol (96:4) to afford an additional 5.5 g. The combined yield of compound (I) as the sodium salt was thus 38.5 g; m.p. 176°-180° C.; $[alpha]_D^{25} = 45.9°$ (c=1, methanol).

Anal. Calcd. for $C_{47}H_{77}O_{14}Na.H_2O$: C, 62.21; H, 8.78.

Found : C, 62.27; H, 8.61.

C-13 nmr (chemical shift (ppm) in $CDCl_3$ with number of attached hydrogens in parentheses): 206.2(0), 183.7(0), 144.9(1), 133.6(0), 110.8(0), 106.8(0), 102.9(1), 99.5(0), 86.3(0), 82.2(1), 80.4(1), 80.3(1), 78.9(1), 74.7(1), 72.2(1), 70.8(1), 69.9(1), 65.4(2), 56.8(3), 44.2(1), 41.6(2), 40.3(1), 39.8(2), 39.5(1), 37.8(1), 36.0(1), 36.0(1), 35.7(1), 34.1(2), 32.5(2), 30.5(2), 30.0(1), 29.8 (2), 27.4(2), 26.8(2), 26.8(3), 19.7(3), 18.6(2), 18.3(3), 16.8(3), 15.0(3), 14.3(3), 13.3(3), 13.2(3), 12.4(3), 11.2(3) and 10.0(3).

The free acid form of antibiotic compound (I) was prepared by vigorously shaking a chloroform solution of the sodium salt with an equal volume of hydrochloric acid at pH 2 in a separatory funnel. The phases were separated and the chloroform layer was washed with water and then evaporated under vacuum to give the free acid; m.p. 98°–102° C. [alpha]$_D^{25}$=27.1° (c=1, methanol);

u.v. (methanol) lambda$_{max}$ at 231 nm (epsilon 14,134).
Anal. Calcd. for $C_{47}H_{78}O_{14}.H_2O$: C, 63.78; H, 9.11.
Found : C, 64.05; H, 9.07.

To reconvert to the sodium salt the free acid (118 mg) was dissolved in 49 ml of methanol and made alkaline to pH 8 using 1N NaOH. The solution was allowed to stir for 30 minutes and was then placed in a separatory funnel and vigorously shaken for several minutes. The solvent was evaporated under vacuum leaving a solid. The solid was dissolved in chloroform and washed with water. The organic phase was separated and evaporated under vacuum to afford a white solid. The spectral properties and analytical data were identical with those found for the sodium salt obtained directly from fermentation as described above.

To prepare the rubidium salt of the antibiotic compound of the formula (I), the free acid (120 mg) was dissolved in 49 ml. of chloroform. Rubidium carbonate (150 mg in 49 ml of water) was added to the chloroform and the mixture was shaken vigorously in a separatory funnel for approximately 5 minutes. The organic phase was separated and extracted one time with water, and then evaporated to afford a white solid. The rubidium salt was recrystallized by slow evaporation from diethyl ether—hexane and the X-ray structure was determined on the resulting crystals by Dr. J. Bordner.

To prepare the potassium salt of the antibiotic compound of the formula (I), the free acid (prepared from 214 mg of the sodium salt as described above) was dissolved in 90 ml of methanol and made alkaline to pH 8 using 1N KOH. The solution was allowed to stir for 15 minutes and was then placed in a separatory funnel and vigorously shaken for several minutes. The solvent was evaporated under vacuum leaving a solid. The solid was dissolved in chloroform and washed with water. The organic phase was separated and evaporated under vacuum to afford 202 mg of compound (I) as the potassium salt: m.p. 172°–175° C.; [alpha]$_D^{25}$=+36.7° (c=1, methanol).

Anal. Calcd. for $C_{47}H_{77}O_{14}K.2H_2O$: C, 59.98; H, 8.67.
Found : C, 59.87; H, 8.71.

We claim:

1. A compound of the absolute stereochemical formula

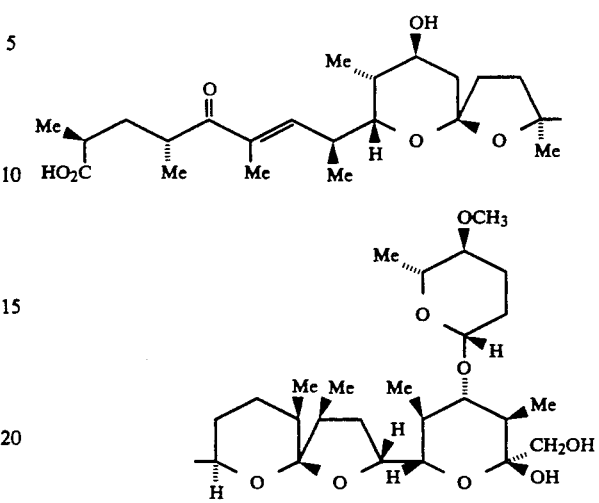

wherein Me=$CH_3$, or a pharmaceutically acceptable cationic salt thereof.

2. The compound of claim 1 in the form of its sodium or potassium salt.

3. A nutrient feed composition for cattle or swine which comprises the compound of claim 1 in an amount effective to promote growth and/or improve feed utilization of said cattle or swine.

4. A method for promoting growth and/or increasing the efficiency of feed utilization in swine or cattle which comprises administering to said swine or cattle a growth promoting or feed-utilization efficiency promoting amount of the compound of claim 1.

5. A method of claim 4 wherein the compound is administered in the form of a nutrient feed composition.

6. A nutrient feed composition for poultry which comprises a compound of claim 1 in an amount effective to control coccidial infections in said poultry.

7. A method for controlling coccidial infections in poultry which comprises administering to said poultry an anticoccidially effective amount of the compound of claim 1.

8. A method of claim 7 wherein the compound is administered to said poultry in the form of a nutrient feed composition.

* * * * *